United States Patent
Iizumi et al.

(10) Patent No.: US 9,206,462 B2
(45) Date of Patent: Dec. 8, 2015

(54) DEVICE FOR BACTERIA CLASSIFICATION AND PRETREATMENT DEVICE FOR BACTERIA TEST

(71) Applicant: HITACHI HIGH-TECHNOLOGIES CORPORATION, Tokyo (JP)

(72) Inventors: Noriko Iizumi, Hitachinaka (JP); Akira Maekawa, Hitachinaka (JP)

(73) Assignee: HITACHI HIGH-TECHNOLOGIES CORPORATION, Tokyo (JP)

(*) Notice: Subject to any disclaimer, the term of this patent is extended or adjusted under 35 U.S.C. 154(b) by 0 days.

(21) Appl. No.: 14/556,603

(22) Filed: Dec. 1, 2014

(65) Prior Publication Data

US 2015/0087017 A1    Mar. 26, 2015

Related U.S. Application Data

(63) Continuation of application No. 13/389,824, filed as application No. PCT/JP2010/003413 on May 21, 2010, now abandoned.

(30) Foreign Application Priority Data

Sep. 8, 2009   (JP) .................................. 2009-206578

(51) Int. Cl.
   *C12Q 1/04* (2006.01)
   *C12M 1/34* (2006.01)

(52) U.S. Cl.
   CPC . *C12Q 1/04* (2013.01); *C12M 41/46* (2013.01)

(58) Field of Classification Search
   CPC ............ C12Q 1/04; C12M 1/22; C12M 1/20; B01L 3/50853; B01L 2300/0822; B01L 3/5027
   USPC ............................................. 435/283.1–309.4
   See application file for complete search history.

(56) References Cited

U.S. PATENT DOCUMENTS

2008/0040044 A1 *   2/2008   Dunlay et al. .................. 702/19

FOREIGN PATENT DOCUMENTS

| JP | 62-155079 | 7/1987 |
|---|---|---|
| JP | 7-286954 | 10/1995 |
| JP | 8-511676 | 12/1996 |
| JP | 2000-258335 | 9/2000 |
| JP | 2001-157572 | 6/2001 |
| JP | 2001-174417 | 6/2001 |
| JP | 2008-17845 | 1/2008 |
| JP | 2009-157028 | 7/2009 |
| WO | WO 9321511 | 10/1993 |

* cited by examiner

*Primary Examiner* — Nathan Bowers
*Assistant Examiner* — Lydia Edwards
(74) *Attorney, Agent, or Firm* — Baker Botts L.L.P.

(57) ABSTRACT

When automatically classified results are different from judgment of a laboratory technician, the laboratory technician has to reselect the bacterial colonies one-by-one to be a pickup colony through watching the displayed image. To get rid of the inconvenience, provided is a pretreatment device for a bacteria test comprising: a specification unit by which an operator instructs to specify the number of bacterial colonies and the increased/decreased number of the bacterial colonies to be displayed; and a display unit for displaying classification results obtained following the operator's instruction. The pretreatment device for a bacteria test facilitates the automatically classified results to be brought close to the judgment of the laboratory technician, resulting in the saving of the time required for checking the appropriate bacterial colonies for the pickup colony.

8 Claims, 9 Drawing Sheets

FIG.9 though often causing the cases that the classified results by the auto-
matic classification are different from the classified results by
the laboratory technician.

DEVICE FOR BACTERIA CLASSIFICATION AND PRETREATMENT DEVICE FOR BACTERIA TEST

CLAIM OF PRIORITY

This application is a continuation of application Ser. No. 13/389,824, filed on Feb. 10, 2012, now pending, which claims the benefit of Japanese Application No. JP 2009-206578, filed Sep. 8, 2009, in the Japanese Patent Office, and PCT Application PCT/JP2010/003413 filed May 21, 2010, the disclosures of which are incorporated herein by reference.

FIELD OF THE INVENTION

The present invention relates to a device for imaging multiple species of bacterial colonies, mixedly cultivated on a culture medium, especially, in a petri dish, and classifying the bacterial colonies into a pickup colony based on the image of the bacterial colonies. The device is applied to a pretreatment of a diagnostic sample for a bacteria test such as infection or antibacterial sensitivity test diagnoses.

BACKGROUND OF THE INVENTION

In the infection therapy, the processes of identifying infecting bacteria, rapidly measuring sensitivity of a patient against antibiotics, and determining an antibiotic to make a treatment plan, are important for the appropriate antibiotics treatment.

In a general procedure, the following flow is performed including the processes of: applying a submitted sample to a culture medium and cultivating bacteria; preparing a bacterial suspension by picking up bacterial colonies thus formed and suspending the bacterial colonies in saline or the like; and inoculating the bacterial colonies with a measurement device of an identification/drug sensitivity test apparatus. In the identification/drug sensitivity test, it is essential to accurately and reproducibly have the bacterial amount inoculated with the measurement device kept constant in the predetermined concentration so as to obtain accurate results.

In many cases, in order to obtain a predetermined bacterial amount, the following procedure is performed including the steps of: picking up a colony by selecting a same species of multiple bacterial colonies from the bacterial colonies grown-up in a petri dish; suspending the selected bacterial colonies in a liquid such as saline, in a single vessel; and measuring turbidity or clouding of the liquid, thereby to prepare a suspension with a predetermined bacterial concentration (or the predetermined number of bacteria).

Herein, the species of the bacterial colonies to be mixed have to be the same. However, multiple species of bacterial colonies generally have grown in the same petri dish. This may demand a high level of a technique for a laboratory technician to select the same species of bacterial colonies from the multiple species thereof. Further, the selection of the multiple bacterial colonies from a variety of large and small colony sizes may require an addition of the bacterial colonies or saline for dilution so as to prepare a test liquid with the predetermined turbidity, even after a test liquid has been once prepared. When the addition of the bacterial colonies is needed, it is necessary to put the sample in the incubator again and wait for the growth of the bacteria, resulting in the requirement of a complicated operation and time. Moreover, those processes are needed to be conducted in large amounts at a large-scale hospital or the like, which leads to a strong demand for an automation apparatus and procedure.

For example, the patent document 1 discloses an apparatus for recognizing positions of bacterial colonies on a petri dish. The apparatus is basically comprised of an automatic recognition unit for recognizing positions of bacterial colonies by using a CCD camera or the like. Then, based on the positional recognition, a tool for collecting bacterial colonies, controlled by an XYZ motor, collects the bacterial colonies. This enables the apparatus to recognize spatial positions of the cultivated bacterial colonies on the petri dish, resulting in the automatic collection of the bacterial colonies by operating a colony collecting pin.

Further, in a bacterial colonies classification, a bacterial colony counter or the like is provided, performing computer processing of feature quantities including color data such as brightness and saturation, and shape or outline data such as degree of an area and a perfect circle, from the image of the individual bacterial colonies, thereby to calculate respective values of the feature quantities. Then, the bacterial colony counter classifies the bacterial colonies depending on the respective values and displays the classified bacterial colonies. Such an apparatus uses a method for having each feature quantity individually specified, as a procedure that a laboratory technician adjusts the classified results shown by the computer.

PRIOR ART DOCUMENTS

Patent Literatures

[Patent Document 1] Japanese Unexamined Patent Application Publication No. 2001-157572
[Patent Document 2] Japanese Unexamined Patent Application Publication No. 2001-174417
[Patent Document 3] Japanese Unexamined Patent Application Publication No. H07-286954
[Patent Document 4] Japanese Unexamined Patent Application Publication No. 2000-258335
[Patent Document 5] Japanese Unexamined Patent Application Publication No. 2009-157028

DISCLOSURE OF THE INVENTION

Problems to be Solved by the Invention

In order to output accurate results through efficiently processing large amounts of samples in an identification/sensitivity test, the automatic processing of recognizing bacterial colonies cultivated in a mixed condition on a petri dish to classify the bacterial colonies under bacteria species or in every appearance, must be conducted with the same accuracy as the operation by a laboratory technician. For this purpose, classification by using a computer is conducted based on the optical features such as hue and saturation or the like, which each bacterial colony has. However, the bacterial colonies having indefinite features, are hard to be classified, thereby often causing the cases that the classified results by the automatic classification are different from the classified results by the laboratory technician.

As mentioned above, when the automatic apparatus outputs the classified results which are unintended by the laboratory technician, the laboratory technician has to manually instruct the apparatus one-by-one to select the bacterial colonies for picking up a colony. Alternatively, in such a case, the laboratory technician needs to bring the classified results close to the predetermined data by individually modulating the value of the feature quantity used by the computer for the classification. This process has prevented the efficient operation by automation from being more improved.

Further, even though the automatically classified results of the bacterial colonies in the petri dish come near the classification of the laboratory technician, if the sufficient number of the bacterial colonies, which meets the predetermined turbidity, is not displayed, the laboratory technician has to again cultivate the bacteria to increase the bacterial colonies through taking the time, resulting in the consumption of time and effort.

Moreover, in order to secure the reliability of the results on the identification/drug sensitivity test, it is needed to have the apparatus capable of being traced on the bacterial colonies collected when the bacterial suspension was prepared. However, the conditions and the images for classifying the bacterial colonies were not stored per every sample.

From the viewpoint of the drawbacks as mentioned above, a first object of the present invention is to provide a device for bacteria classification and a pretreatment device for a bacteria test, usable in a convenient operational procedure and processing thereof so as to bring the automatically classified results close to the classification conducted by a laboratory technician.

Further, a second object of the present invention is to provide a device for bacteria classification and a pretreatment device for a bacteria test, including an operational unit and processing the increase or decease in the number of the bacterial colonies as a candidate of a pickup colony in the same classification, thereby to display an image of the bacterial colonies. Note those operations can be performed without cultivating the bacterial colonies by spending more cultivating time, if the number of the pickup colony is intended to increase or decrease in order to prepare the bacterial suspension which meets the predetermined turbidity.

Moreover, a third object of the present invention is to provide a device for bacteria classification and a pretreatment device for a bacteria test, which store the traceability data on the preparation of a bacterial suspension supplied to the identification/drug sensitivity test.

Means for Solving the Problems

In order to accomplish the above mentioned objects, a pretreatment device for a bacteria test of the present invention comprises: an imaging unit for taking an image in a petri dish; a display unit for displaying the image in the petri dish; an automatic detection/classification unit for detecting/classifying the bacterial colonies in the petri dish; a display unit for displaying the detected and classified bacterial colonies in the petri dish; a selection unit for selecting the bacterial colonies in the petri dish; and a pickup colony unit for fishing the selected bacterial colonies in the petri dish.

Further, the pretreatment device for a bacteria test comprises: an input unit for inputting the classification number of the bacterial colonies; an input unit for inputting increase or decrease in the classification number of the pretreatment device for a bacteria test; an extraction/display unit for extracting and displaying the bacterial colonies with the specified classification number of the bacterial colonies; an MD calculation processing unit for calculating a Mahalanobis' generalized distance by the individual feature quantity of each bacterial colony; a classification processing unit for increasing or decreasing the number of the displayed bacterial colonies while modulating a threshold of the classification of the bacterial colonies to keep the specified classification number; and a history storage unit for storing classification conditions and classification results while classifying the bacterial colonies as a history thereof.

Advantageous Effects of the Invention

The devices of the present invention facilitate the automatically classified results of the bacterial colonies in the petri dish for picking up a colony or the like to be brought close to the judgment of the laboratory technician, thereby allowing the operation of checking the appropriate pickup colony to be easily performed. Particularly, when the bacteria species in the petri dish are almost determined, the number of the bacteria species may be specified in advance. This enables a laboratory technician to reduce a load of the checking operation for the pickup colony, thereby to improve the throughput of the pretreatment for a bacteria test. Further, under the condition of the same classification number, the number of the bacterial colonies to be a candidate of the pickup colony may be increased or decreased. This allows a collection of sufficient amounts of bacteria or a collection of only absolute bacteria to be easily instructed. Therefore, it becomes possible to omit the time for increasing the number of the bacterial colonies consumed by recultivating the colonies again, and improve the reliability of the bacterial colonies to be collected. Moreover, the combinational storage of both classification results in bacterial colonies modulated by the aforementioned operation and classification conditions may secure the traceability of the identification/drug sensitivity test.

BEST MODE FOR CARRYING OUT THE INVENTION

The best mode for carrying out the present invention will be shown hereinafter. Note the present embodiment will be explained only to understand the present invention. Therefore, the present invention is not limited to the embodiment described hereinafter and various modifications may be applied.

Hereinafter, an embodiment showing an example of the present invention will be explained, referring to the attached drawings.

Figure 1:
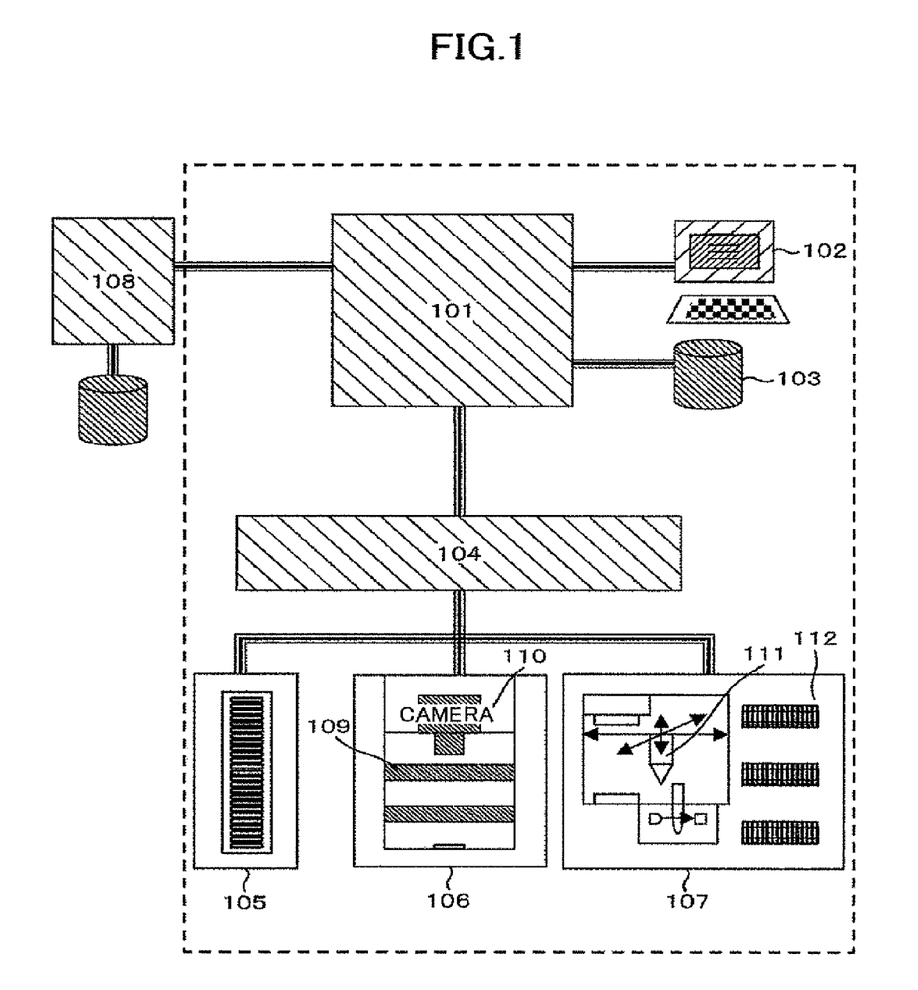
FIG. 1 is a block diagram showing a whole construction of the device according to an embodiment of the present invention.

FIG. 1 is a diagram showing a whole construction of a pretreatment device for a bacteria test to which the present invention is effectively applied.

First, a sample collected from a biological sample of a test subject is applied to each culture medium in every petri dish. Then, a laboratory technician places the petri dishes where the bacterial colonies are grown up, at a sample supply/transport unit 105. Each petri dish is transported to an imaging unit 106, thereby to take images thereof using a camera 110 illuminated by a light 109. Herein, the images taken at this time are collected as a plurality of images needed for the image processing conducted in the later process, through modifying an angle of the light 109 and an illumination method. Further, low-angle illumination, high-angle illumination, and a transmission type of illumination are used by the light 109, depending on the necessity.

The collected images are transferred from a control unit computer 104 to an operation unit computer 101. Then, the petri dish in which image has been collected is moved to a picking up colonies and preparing suspension unit 107. Simultaneously, the operation unit computer 101 detects the individual positions of the bacterial colonies existing in the petri dish based on the collected images, and classifies the bacterial colonies. The classification results are displayed on an operation console 102.

The laboratory technician observes the classification results, and instructs the selection of the bacterial colonies for pickup colony. The operation computer 101 calculates the coordinates of all the bacterial colonies for pickup colony, specified by the laboratory technician, and transfers the data thus calculated to the picking up colonies and preparing suspension unit 107.

As mentioned above, the specified bacterial colonies are fished by using a pickup colony rod 111 from the petri dish which was moved to the picking up colonies and preparing suspension unit 107, whereby a bacterial suspension 112 is prepared. The petri dishes after the pickup colony process are housed in a sample supply/transport unit 105.

Among the aforementioned operations, the sample supply/transport unit 105, the imaging unit 106, and the picking up colonies and preparing suspension unit 107 are integratedly controlled by the control unit computer 104. Further, the data showing the processes by a process of modulating the bacterial suspension, including the collected images or the detected coordinates of the bacterial colonies, are stored in a history storage unit 103. Then, the data are transmitted to an outside system 108 where necessary. Furthermore, the outside system 108 and the operation unit computer 101 also communicate with each other on the sample data or the like.

Figure 2:
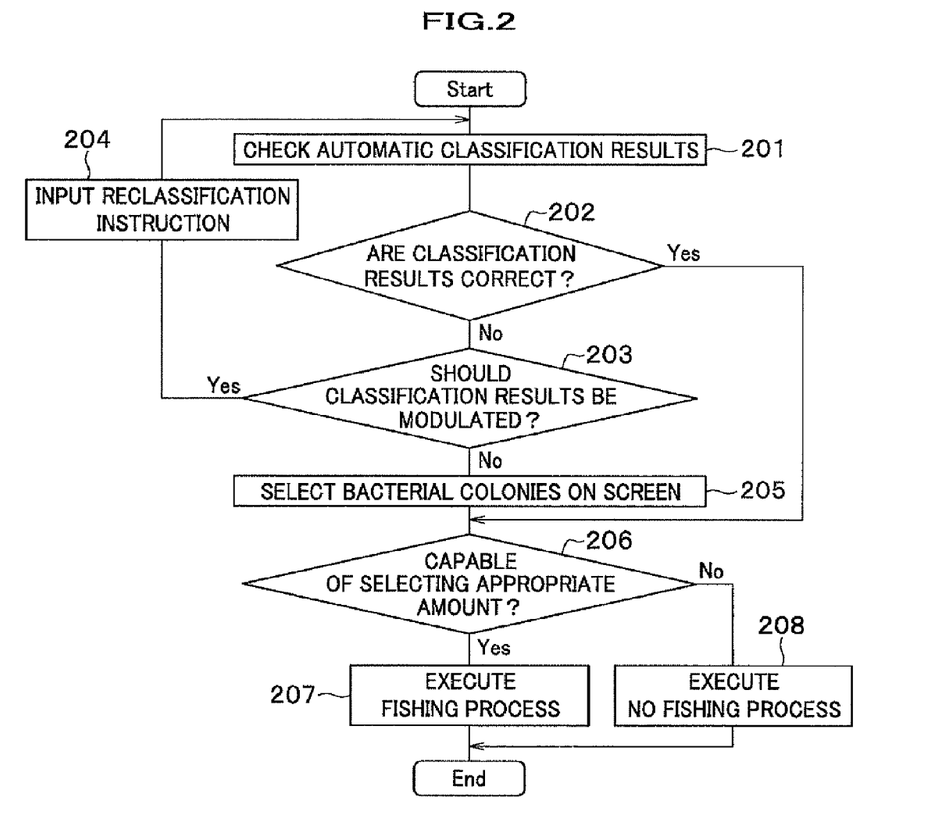
FIG. 2 is a flowchart showing an example of the operational flow when the cultivated bacteria are selected for the purpose of picking up a colony or the like according to an embodiment of the present invention.

Next, an example of the conventional operation will be explained referring to FIG. 2, when a laboratory technician instructs to select the bacterial colonies for the purpose of pickup colony, by using the pretreatment device for a bacteria test of the present invention.

First, the laboratory technician observes the automatically detected/classified image through the operation console 102, and checks whether or not the classification results are the same as the judgment of the laboratory technician (step 201). If the automatically classified results are different from the judgment of the laboratory technician (step 202), the laboratory technician judges whether or not the automatically classified results should be modulated (step 203). If the laboratory technician modulates the classified results, the laboratory technician inputs the instruction for reclassification through the operation console 102 (step 204). The operation unit computer 101 displays again the reclassified results following the inputted instruction. The processing from the step 201 to the step 204 is repeatedly executed until the reclassified results are consistent with the judgment of the laboratory technician. However, if the reclassified results are continuously still inconsistent with the judgment of the laboratory technician, the laboratory technician stops the reclassification processing, and may select the bacterial colony one-by-one, which should be fished as a target, through watching the display screen (step 205).

As mentioned above, when the laboratory technician has finished the selection of the bacterial colonies for the pickup colony, the laboratory technician checks whether or not there are the appropriate number (or amount) of the bacterial colonies for preparing a bacterial suspension (step 206). If the appropriate amount of the bacterial colonies is selected, the laboratory technician instructs the pickup colony (step 207). In contrast, if the appropriate amount of the bacterial colonies is not selected, it is useless to perform the fishing treatment. Accordingly, the laboratory technician instructs not to perform the fishing treatment (step 208). As mentioned hereinbefore, the laboratory technician performs a series of the treatments with respect to all the samples.

On the contrary, next, a procedure of modulating the automatically detected/classified results will be explained. Note this is the essential functionality of the present invention.

Figure 3:
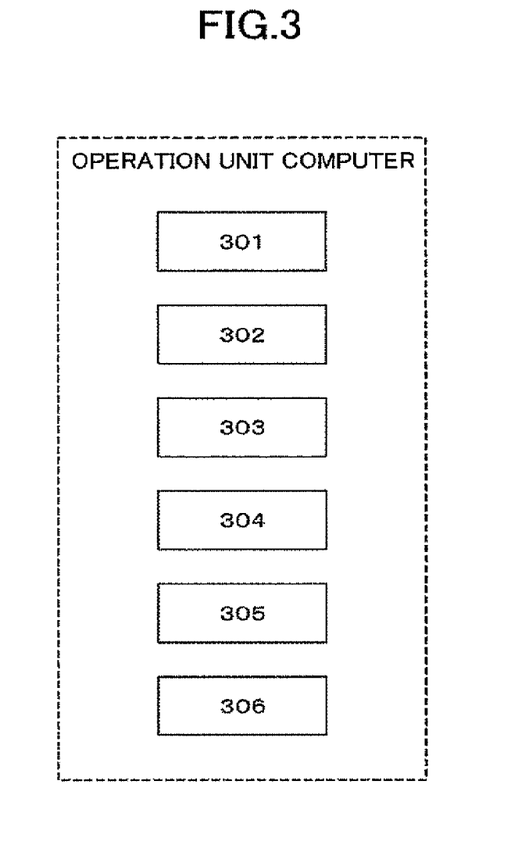
FIG. 3 is a block diagram showing processing executed in a computer of an operation unit according to an embodiment of the present invention.

First, a construction of the processing unit in the operation unit computer 101 will be explained referring to FIG. 3. A data input/output unit 301 inputs/outputs data into/from the operation console 102, the history storage unit 103, the control unit computer 104, and the outside system 108. A bacterial colonies image processing unit 302 detects an isolated bacterial colony or calculates coordinates of the individual bacterial colonies, based on the image in the petri dish. A bacterial colonies classification processing unit 303 extracts feature quantities of all the bacterial colonies detected by the bacterial colonies image processing unit 302, thereby to classify the bacterial colonies. The processing unit for modulating the displayed number of bacterial colonies 304 modulates a threshold according to degree of the displayed number instructed by the laboratory technician, and subsequently extracts the bacterial colonies as display targets. The bacterial colonies classification processing unit 303 and the processing unit for modulating the displayed number of bacterial colonies 304 will be explained in detail hereinafter.

An MD calculation processing unit 305 calculates a Mahalanobis' generalized distance (or MD) based on a plurality of feature quantities of the bacterial colonies. A history data processing unit 306 stores data of classification conditions and classified results of the bacterial colonies per sample into the history storage unit 103.

Then, when the classified results processed by the operation unit computer 101 are different from the judgment of the laboratory technician, will be explained a procedure for specifying the classification number and having the computer's classified results come near the desired results.

Figure 4:
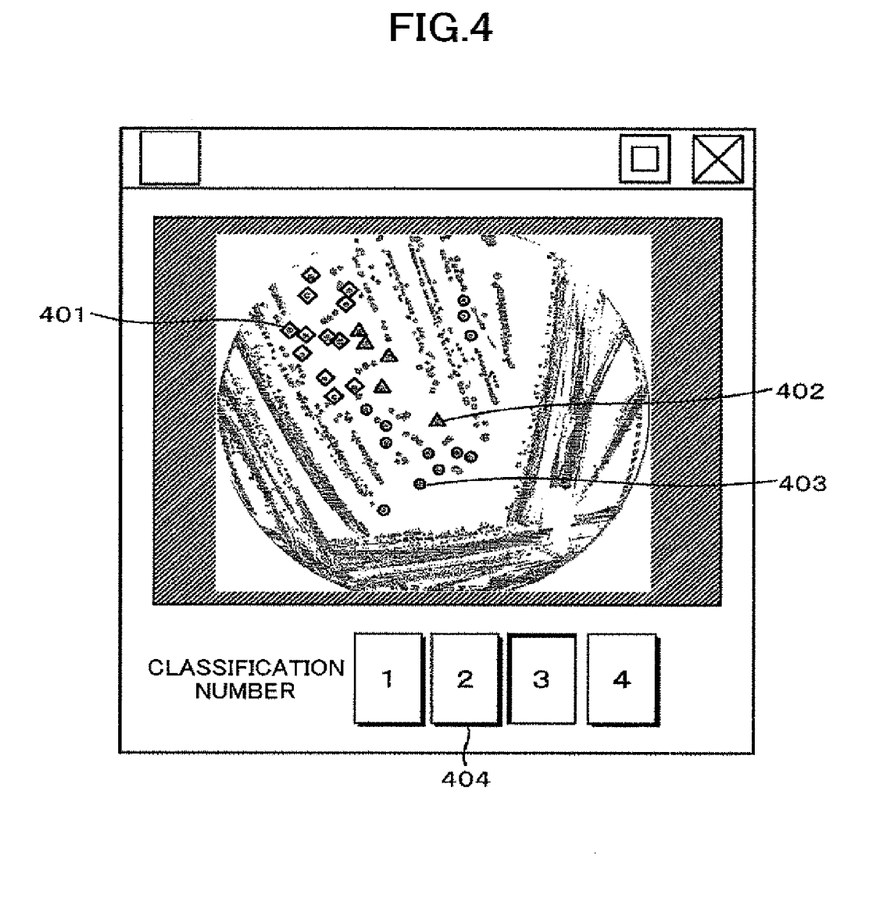
FIG. 4 is a diagram showing an example of a screen for displaying classification results to an operator so as to have the operator specify the classification number according to an embodiment of the present invention.

First, the laboratory technician who has checked the image displayed on the operation console 102 inputs the classification number through the screen as shown in FIG. 4. FIG. 4 shows a result that the bacterial colonies are classified into three types (that is, type 401 to type 403). In contrast, when the laboratory technician wants to display a result that the bacterial colonies are classified into two types, "2" is inputted through the classification number specifying button 404. Hereby, the bacterial colonies classification processing unit 303 executes again the classification processing, thereby to display the bacterial colonies in the specified classification number of 2, as shown in FIG. 5.

Here, will be explained an example that the bacterial colonies classification processing unit 303 classifies the bacterial colonies following the specified classification number. In order to classify the bacterial colonies, a large quantity of data should be collected beforehand, and the feature quantities are needed to be extracted. In the case of the bacterial colonies, the feature quantities are defined as color data such as brightness and saturation, and a shape and an outline such as an area and degree of a perfect circle. Then, these feature quantities are subjected to a multivariate analysis, so as to generate a distribution space of the classification. A method for a multivariate analysis includes a clustering analysis and a pattern recognition analysis using a Mahalanobis' generalized distance. Usually, various types of groups exist in the distribution space to be generated. Using the phenomenon, the bacterial colonies classification processing unit 303 judges whether or not there are the bacterial colonies to be classified as the pickup colony, and displays the classified results on the operation console 102. In general, the number of the bacterial colony types existing in the petri dish is different per each sample. Thus, the laboratory technician does not know the classification number from the beginning. Therefore, there is a case that the bacterial colonies are classified in a more detailed manner or in a rougher manner. Then, the laboratory technician specifies the preferable classification number through the classification number specifying button 404. After that, the bacterial colonies classification processing unit 303 conducts reclassification processing such that the classification number becomes the specified classification number.

Figure 5:
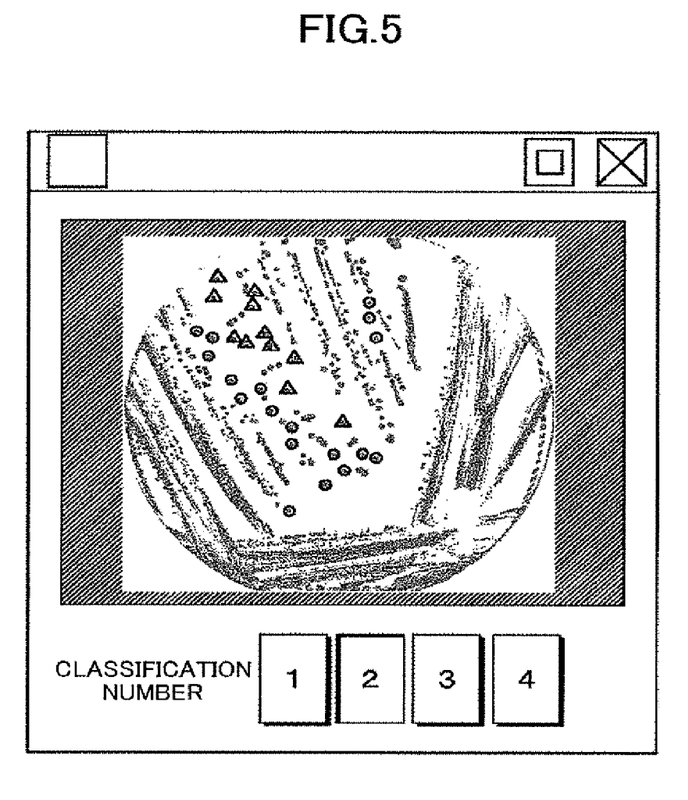
FIG. 5 is a diagram showing an example of redisplaying the bacterial colonies on the screen, following the classification number specified by the operator according to an embodiment of the present invention.

FIG. 5 shows the image of the bacterial colonies, which were firstly classified into three groups and secondly reclassified into two groups. If adjacent groups exist in the distribution space generated beforehand, such a grouping becomes possible. Whether adjacent groups exist or not is determined by setting a predetermined threshold. This may prevent the groups having very different features from being displayed to be classified into one classification group on a screen.

As mentioned above, the laboratory technician may specify the classification number to modulate the classification results, instead of one-by-one modulating the features on the appearance of the image.

Next, a procedure for obtaining the desirable classification results will be explained, by specifying the classification number in advance.

Figure 6:
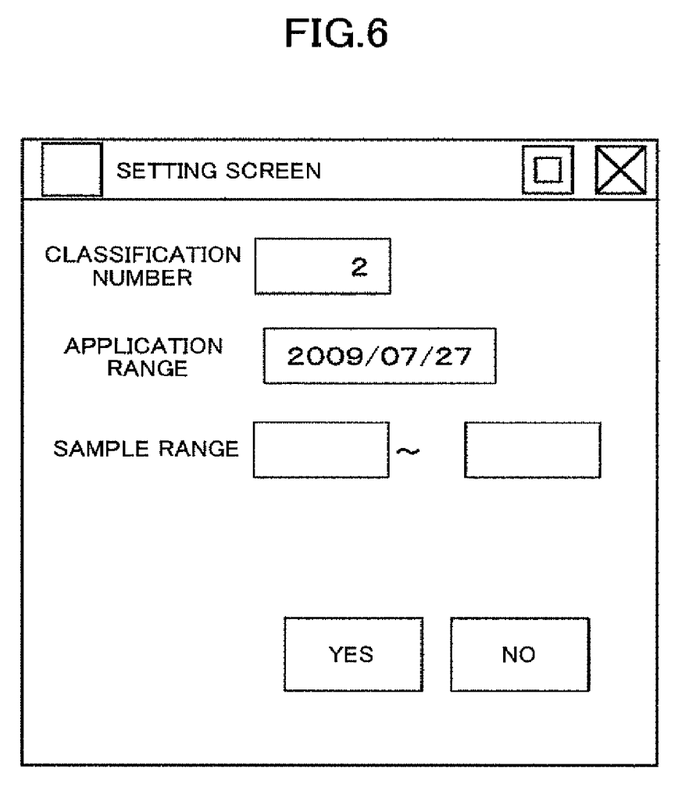
FIG. 6 is a diagram showing an example of the screen for having the operator set the classification number in advance according to an embodiment of the present invention.

Usually, multiple species of bacterial colonies are growing in a single petri dish for a bacteria test. However, depending on the operation, there is a case that a species of the cultivated bacterial colonies is already determined. For example, on a unique culture medium, called a selective medium, only specific bacteria are selectively growing. When the petri dishes under such a condition are sequentially pretreated, the classification number is made to be set in advance through a setting screen shown in FIG. 6. Hereby, the bacterial colonies classification processing unit 303 judges whether or not the treated target sample falls under the setting. If the treated target sample falls under the above mentioned setting, the results classified by the aforementioned data are displayed on the operation console 102 as the first classification results. Herein, the classification number set in advance and the data relevant to the targets may be inputted from the outside system as a part of the sample data.

The above mentioned procedure allows the classification results close to the judgment of the laboratory technician to be initially displayed by using the known data beforehand.

Next, will be explained a procedure for modulating the amount of bacterial colonies for pickup colony so as to have the bacterial suspension show the predetermined turbidity, after the laboratory technician has checked the classification results of the bacterial colonies in the petri dish.

Figure 7A:
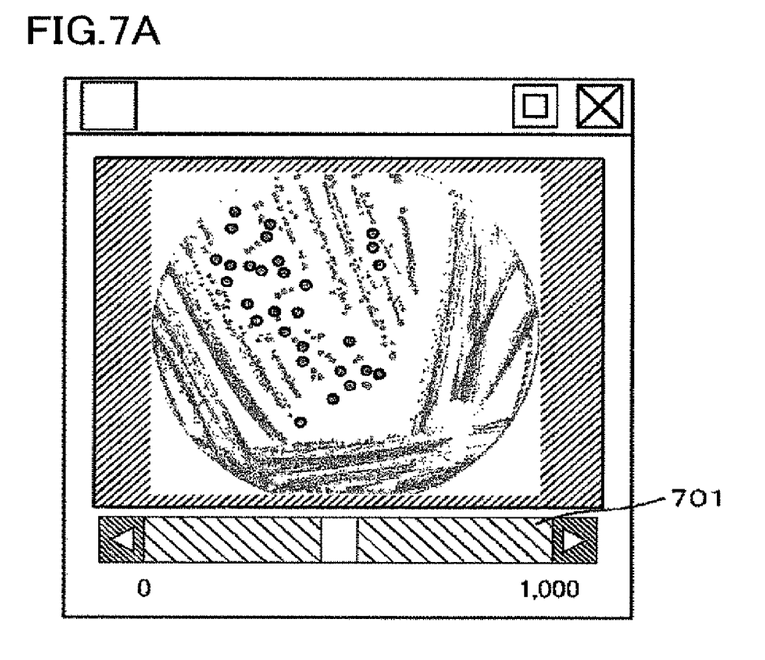
FIGS. 7A and 7B are diagrams each showing an example of having the operator specify the increase or decrease in the number of the bacterial colonies to be displayed, and following the specification, of modulating the number of the bacterial colonies thereby to redisplay a modified image of the bacterial colonies, according to an embodiment of the present invention.
Figure 7B:
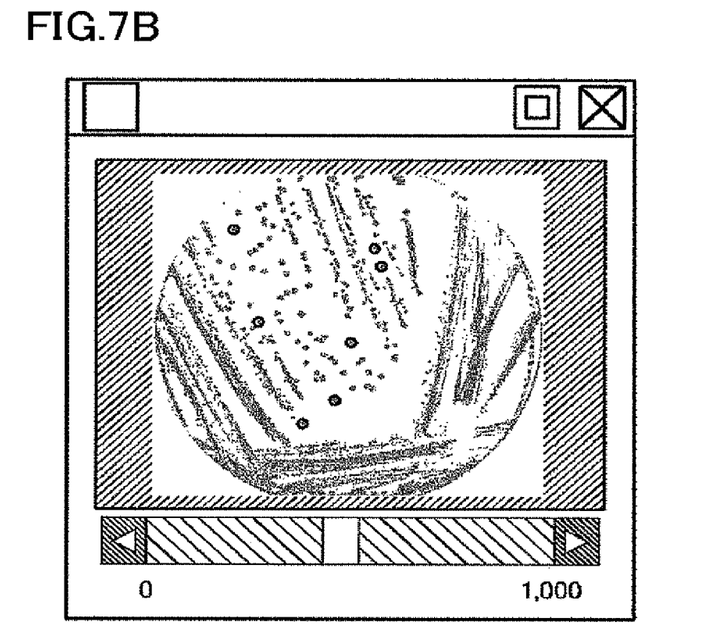

Here, even though the bacterial colonies in the petri dish are classified and modulated exactly as a vision of the laboratory technician, there may be a case that the number (or amount) of the bacterial colonies becomes insufficient for preparing a bacterial suspension. Conversely, there is a case that the bacterial colonies must be carefully selected due to the too many number (or much amount) thereof. Hereby, without changing the modification number, in order to increase/decrease the number of the bacterial colonies to be the pickup colony, a modulation control 701 shown in FIGS. 7A and 7B sequentially specifies the increase/decrease in the number of the bacterial colonies based on the presently displaying classification. When the increase/decrease in the number of the bacterial colonies is specified, a processing unit for modulating the displayed number of bacterial colonies 304 increases/decreases a threshold which is a belonging degree of the displaying bacterial colonies to a specific bacterial colony group. An MD calculated by an MD calculation processing unit 305 with respect to the individual bacterial colonies represents a belonging degree of the individual bacterial colonies to the specific colony group. Accordingly, if the usually displayed threshold is set to 4, in the range where the minimum value of the threshold is set to 0 and the maximum value thereof is set to 1,000, in accordance with the increased/decreased degree specified by the laboratory technician, the threshold of the displaying bacterial colonies is modulated, and the modulated threshold is displayed on the operation console 102. Herein, FIG. 7B shows an exemplary screen of the case that the displaying number of the bacterial colonies in FIG. 7A is instructed to be decreased.

The above mentioned procedure allows the display of the number of the bacterial colonies for the pickup colony to be easily modulated.

Figure 8:
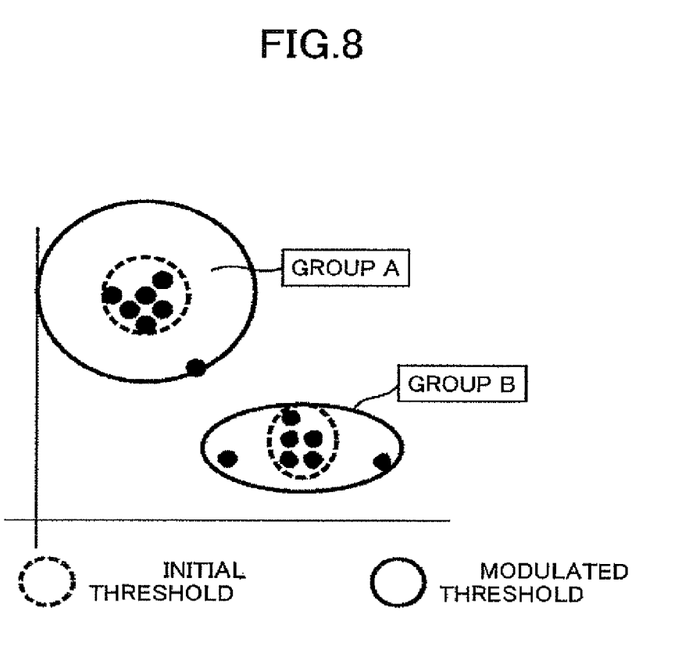
FIG. 8 is a spatially distributional diagram showing the increase or decrease number of the candidate bacterial colonies, caused by modifying a threshold.

Here, the increase/decrease of the bacterial colony number explained hereinbefore will be further described complementally. Assuming that a certain group in the distribution space is focused, the belonging (or attribution) degree to the focused group is made to be modulated by the threshold. For example, as shown in FIG. 8, the threshold defined by the inside region surrounded by the initial circle represents that a group A has six colonies and a group B has five colonies. Herein, the modulation of the threshold enables the number of the colonies to be changed so that the group A has seven colonies and the group B has seven colonies. Further, the weighting on the feature quantities of N colonies allows the surrounding shape (or range) of the threshold to be modified.

Finally, will be explained a procedure for storing the traceability data on preparing a bacterial suspension supplied to an identification/drug sensitivity test.

According to the procedures or the like described hereinbefore, the classification results displayed on the operation console 102 turns to be modified. A history data processing unit 306 manages the data on what conditions were used to classify the bacterial colonies, and which bacterial colonies were fished, and stores those data together with the image data in the history storage unit 103. The data are stored per petri dish unit, so that the classification number and the total number of the displaying bacterial colonies as well as the date and the time, and the sample data are stored. Then, the threshold, the displaying bacterial colony number, and the bacterial colony number for the pickup colony, when they are displayed, are also stored in the history storage unit 103 per classified species. Furthermore, the coordinates data of the bacterial colonies for the pickup colony are stored per bacterial colony for the pickup colony. The history data stored in the history storage unit 103 are transmitted to the outside system depending on the necessity, to be utilized for the traceability such as a preparation of a bacterial suspension, and an identification/drug sensitivity test or the like.

Figure 9:
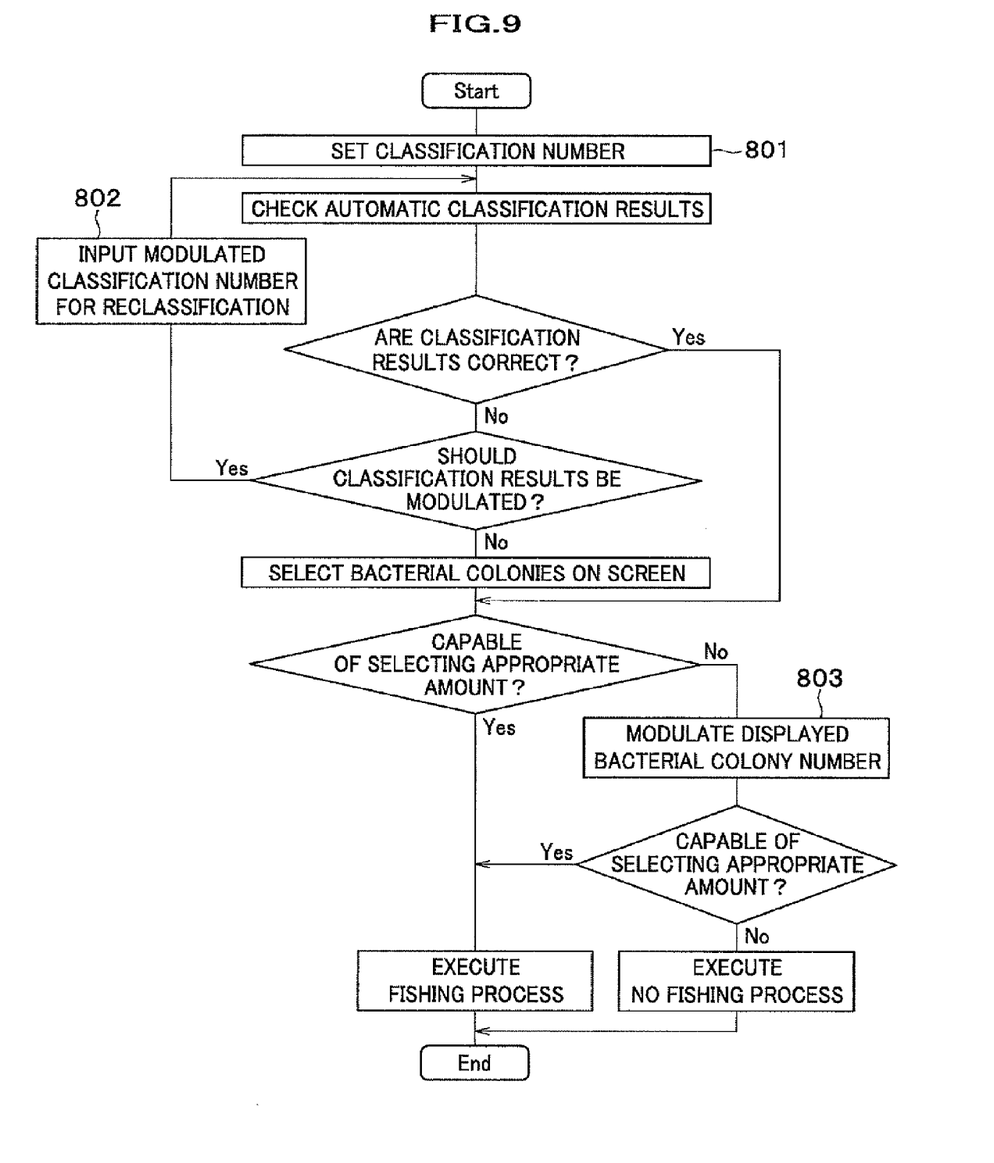
FIG. 9 is a diagram showing an example of a new operational flow when the cultivated bacteria are selected for the purpose of picking up a colony or the like, according to an embodiment of the present invention.

FIG. 9 shows a new operation flow in the pretreatment device for a bacteria test, also comprising the aforementioned units and procedures of the present invention. That is, a prior setting step of the classification number (step 801), an instruction step of the classification number (step 802), and a modulation step of the displaying bacterial colony number (step 803) are newly added. This new flow may reduce the operational load of the laboratory technician.

According to the present invention, the operation for bringing the automatically classified results close to the judgment of the laboratory technician may become easily performed, which results in the saving of the time required for the operation of checking the appropriate bacterial colonies for the pickup colony. Further, the automatically detecting targets may be increased, without cultivating again the bacterial colonies for the pickup colony. The above mentioned advantages allow the throughput of the pretreatment for a bacteria test to be remarkably improved.

Moreover, the pretreatment device for a bacteria test further comprises an instruction unit by which the operator increases/decreases the classification number and the displaying bacteria colony number, and a display unit for displaying the classification results following the operator's instruction, as the automatic detection/classification processing for the bacterial colonies. This allows the intended classification results to be obtained without modulating the individual feature quantities displayed on the screen, if the automatically classified results are different from the judgment of the laboratory technician, resulting in the improvement of the throughput in the pretreatment for a bacteria test.

If the automatically classified results are different from the judgment of the laboratory technician, the operator has to operate the device by modulating the individual feature quantities displayed on the screen so as to bring the automatically classified results close to the desired classification results. Alternatively, the operator has to reselect again the bacterial colonies for the pickup colony one-by-one through watching the displayed screen. Further, if the bacterial colonies are unable to be automatically detected from the bacteria suspension which satisfies the predetermined turbidity, the operator also has to recultivating the bacteria to increase the number (or amount) of the bacteria.

As mentioned hereinbefore, the pretreatment device for a bacteria test is configured to comprise the instruction unit by which the operator increases/decreases the classification number and the displaying bacteria colony number, and the display for displaying the classification results following the operator's instruction.

According to the present invention, the operation for bringing the automatically classified results close to the judgment of the laboratory technician becomes to be easily conducted, resulting in the saving of the time required for the checking operation of the appropriate bacterial colonies for the pickup colony. Further, the automatically detecting targets may be increased, without cultivating again the bacterial colonies for the pickup colony. The above mentioned advantages allow the throughput of the pretreatment for a bacteria test to be remarkably improved.

DESCRIPTION OF REFERENCE NUMERALS

101 Operation unit computer
102 Operation console
103 History storage unit
104 Control unit computer
105 Sample supply/discharge unit
106 Imaging unit
107 Picking up colonies and preparing suspension unit
108 Outside system
109 Illumination
110 Camera
111 Pickup colony rod
112 Bacterial suspension
301 Data input/output unit
302 Bacteria colonies image processing unit
303 Bacterial colonies classification processing unit
304 Processing unit for modulating the displayed number of bacterial colonies
305 MD calculation processing unit
306 History data processing unit

The invention claimed is:

1. A method for bacteria classification using a bacterial classification device, the method comprising the steps of:
   taking an image in a petri dish including bacterial colonies therein by an imaging unit;
   displaying the image in the petri dish by a display unit;
   classifying the bacterial colonies in the petri dish based on color data including brightness and saturation, and a shape and an outline including an area and degree of a perfect circle with respect to each bacterial colony by a classification unit;
   outputting an image which has an operator set the number of the classified bacterial colonies in advance, and then inputting the specified number of the classified bacterial colonies by a data input/output unit; and
   reclassifying the bacterial colonies once classified by the classification unit based on the number of the classified bacterial colonies specified by the operator and the color data including brightness and saturation, and the shape and the outline including the area and degree of the perfect circle with respect to each bacterial colony by a bacterial colonies classification processing unit, wherein
   an instruction for increasing/decreasing the number of candidate bacterial colonies is inputted by the data input/output unit, corresponding to the classification results of the bacterial colonies in the petri dish, in accordance with the number of the classified bacterial colonies specified by the operator;
   the bacterial colonies classification processing unit classifies the bacterial colonies following a specified degree of the increased/decreased number of the bacterial colonies inputted by the data input/output unit; and the bacterial colonies classification processing unit represents the color data including brightness and saturation, and the shape and the outline including the area and degree of the perfect circle with respect to each bacterial colony by a Mahalanobis' generalized distance, thereby to perform the classification by modulating a threshold following the specified degree of the increased/decreased number of the bacterial colonies.

2. The method for bacteria classification as described in claim 1, wherein any of a plurality of groups adjacent in a distribution space that is calculated by a multivariate analysis of the color data including brightness and saturation, and the shape and the outline including the area and degree of the perfect circle with respect to each bacterial colony, are made to be one group, if the number of the classified bacterial colonies needs to be decreased after the bacterial colonies classification processing unit conducts reclassification processing.

3. The method for bacteria classification as described in claim 1, wherein any of a plurality of groups in a distribution space that is calculated by a multivariate analysis of the color data including brightness and saturation, and the shape and the outline including the area and degree of the perfect circle with respect to each bacterial colony, are made to be divided into a plurality of groups, if the number of the classified bacterial colonies needs to be increased after the bacterial colonies classification processing unit conducts reclassification processing.

4. The method for bacteria classification as described in claim 1, further comprising the step of storing the specified number of the classified bacterial colonies and classification results obtained following the specified number of the classified bacterial colonies as history data by a history storage unit.

5. The method for bacteria classification as described in claim 1, wherein the specified degree of the increased/decreased number of the candidate bacterial colonies and classification results obtained following the specified degree thereof are stored as history data.

6. A method for a bacterial test comprising the steps of:
performing the method as described in claim 1;
selecting bacterial colonies in a petri dish by a selection unit; and
picking up the selected bacterial colonies by a pickup colony unit.

7. A method for bacteria classification using a bacteria classification device, the method comprising the steps of:
taking an image in a petri dish by an imaging unit;
displaying the image in the petri dish by a display unit;
picking up bacterial colonies in the petri dish by a pickup colony unit;
outputting an image which has an operator set the number of the classified bacterial colonies in advance, and then input the specified number of the classified bacterial colonies by a data input/output unit configured to; and
classifying the bacterial colonies in the petri dish into the number of classified groups specified by an operator, wherein the classification unit classifies the bacterial colonies by color data including brightness and saturation, and a shape and an outline including an area and degree of a perfect circle with respect to each bacterial colony by a classification unit.

8. A method for a bacterial test comprising the steps of:
performing the method as described in claim 7;
selecting bacterial colonies in a petri dish by a selection unit, wherein the pickup colony unit picks up the selected bacterial colonies.

* * * * *